United States Patent [19]
Kim et al.

[11] Patent Number: 5,481,034
[45] Date of Patent: Jan. 2, 1996

[54] FLUORINATED ABSCISIC ACID DERIVATIVES AND PLANT GROWTH REGULATOR THEREOF

[75] Inventors: Bum-Tae Kim; Yong-Ki Min; No-Kyun Park; Tae-Jun Kim; Kwang-Yun Cho, all of Daejeon, Rep. of Korea

[73] Assignee: Korea Research Institute of Chemical Technology, Daejeon, Rep. of Korea

[21] Appl. No.: 346,520

[22] Filed: Nov. 29, 1994

[30] Foreign Application Priority Data

May 2, 1994 [KR] Rep. of Korea ............... 1994-9591
May 2, 1994 [KR] Rep. of Korea ............... 1994-9592

[51] Int. Cl.$^6$ .................................................. C07C 61/08
[52] U.S. Cl. .................. 562/507; 560/125; 549/330; 549/333; 568/446; 568/823; 504/140; 504/162
[58] Field of Search ..................... 562/507; 560/125; 549/330, 333; 568/441, 823; 504/140, 162

[56] References Cited

PUBLICATIONS

M. Soukup et al., Synthese von(+)—Abscisinsäure, Helvetica Chimica Acta, 72:361–364 (1989).
F. Kienzle et al., Synthese von optisch aktiven, natürlichen Carotinoiden und strukturell verwandten Verbindungen.III. Synthese von(+)—Abscisinsäure, (–)—Xanthoxin, (–)—Loliolid, (–)—Actinidiolid und (–)—Dihydroactinidiolid, Helvetica Chimica Acta, 61:2616–2627 (1978).
T. Kitahara et al., Stereocontrolled Syntheses of Both the Enantiomers of Phaseic Acid and its Methyl Ester, A Pivotal Metabolite of Abscisic Acid, Tetrahedron, 45(20):6387–6400 (1989).
L. A. K. Nelson et al., Synthesis of (+)—, (–)— and (±)—7'—Hydroxyabscisic Acid, Tetrahedron, 47(20/21):3259–3270 (1991).
S. Takahashi et al., Total Synthesis of (±)—Methyl Phaseates, Agric. Biol. Chem., 50(6):1589–1595 (1986).
K. Yamashita et al., Synthesis and Biological Activity of Methyl 3-Demethyl Abscisate and its Related Analogs, Agric, Biol. Chem., 46(12):3069–3073 (1982).

M. G. Constantino et al., An Efficient Synthesis of (±)—Abscisic Acid, J. Org. Chem., 51:253–254 (1986).
D. L. Roberts et al., Synthesis of (RS)—Abscisic Acid, J. Org. Chem., 33:3566–3569 (1968).
R. D. Willows et al., Synthesis and Properties of C–1—azido—ABA, Phytochemistry, 32(4):869–873 (1993).
M. G. Contantino et al., A Novel Synthesis of (±)—Abscisic Acid, J. Org. Chem., 54:681–683 (1989).
N. Lamb et al., Synthesis of Optically Active Cyclohexanone Analogs of the Plant Hormone Abscisic acid, Can. J. Chem., 68:1151–1162 (1990).
B. T. Kim et al., Synthesis of New Abscisic Acid(ABA) Analogs Possessing a Geometrically Rigid Cyclized Side Chain, Biosci. Biotech. Biochem., 56(4):624–629 (1992).
Y. Todoroki et al., 8'— and 9'—Methoxyabscisic Acids as Antimetobolic Analogs of Abscisic Acid, Biosci. Biotech. Biochem., 58(4):707–715 (1994).
N. Lamb et al., Oxidation of the 8'—Position of a Biologically Active Abscisic Acid Analogue, Phytochemistry, 34(4):905–917 (1993).
P. A. Rose et al., Synthesis, Resolution and Biological Activity of 7', 7'—Difluoroabscisic acid, Phytochemistry, 31(4):1105–1110 (1992).

Primary Examiner—Paul J. Killos
Attorney, Agent, or Firm—Darby & Darby

[57] ABSTRACT

The present invention provides novel fluorinated abscisic acid derivative represented by formula of:

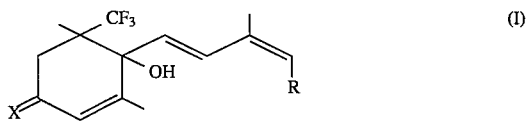

(I)

wherein:
  X is O(CH$_2$)$_2$O or O; and,
  R is hydroxymethyl, aldehyde, C$_{1-2}$ alkoxycarbonyl or carboxyl group.

The present invention also provides a novel process for preparing the fluorinated abscisic acid derivative represented as the formula (I), and also provides their use for plant growth regulator.

2 Claims, No Drawings

FLUORINATED ABSCISIC ACID DERIVATIVES AND PLANT GROWTH REGULATOR THEREOF

FIELD OF THE INVENTION

The present invention relates to novel abscisic acid derivatives, more specifically, to novel fluorinated abscisic acid derivatives, process for preparing same and their use for plant growth regulators.

BACKGROUND OF THE INVENTION

Abscisic acid(hereinafter referred to as "ABA") represented as structural formula below, is one of plant growth hormones natually occurring in plants; and, it is a causal substance of abscission and dormancy in plants. In addition to this, biological activity of ABA is greatly diverse, including inhibition of germination and growth, inhibition of α-amylase induction, inhibition of transpiration, and induction of stomatal closure. ABA has also been found to be a substance inducing anti-stress responses, in a view of the fact that the level of ABA is elevated in plants responding to environmental stresses such as drought and cold temperature.

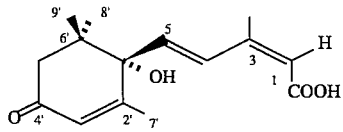

Recently, the structure-activity relationship of ABA has been actively studied by several groups of workers. It is summarized as follows: To possess biological activity, the side chain structure should have carboxylic group, and 2-cis, 4-trans configuration, and methyl group at C-3. In terms of ring system, methyl group and double bond at C-2' are essential. Further, carbon at C-4' should be ketone or be able to be oxidized to become ketone. However, all of ABA analogs having alcohol group instead of carboxylic group, with different configurations, and having no methyl substitution or a longer alkyl group, are less inactive than natural ABA.

Natural or intact ABA, however, has not been developed into a practical plant growth regulator, grounded on the following reasons:

first, natural ABA does not show stable and steady activity, since double bond in side chain is easily isomerized to produce inactivated form; and, secondly, the level of natural ABA cannot be maintained in an effective amount, since it is easily metabolized to biologically inactive phaseic acid.

In this connection, various modifications were made to the structure of ABA to solve the technical task in the art as follows:

Todoroki et al disclose a process for preparing ABA in which C-8' or C-9' methyl group is replaced with a methoxy group; the process, however, requires complex and vigorous reaction condition employing reactant hard to handle such as bromine. Moreover, since isomeric mixture of the methoxy-ABA and biologically inactive 2-trans-4-trans isomer is produced during the hydrolysis step of reaction intermediate, laborous separation step is essentially required to obtain the desired ABA in isolated form. In addition, (+)-9'-methoxy-ABA is more effective than (+)-8'-methoxy-ABA, which is expected to be an antimetabolic analog, suggesting that methoxy group itself might affect the activity(see: Y. Todoroki et al, Biosci. Biotech. Biochem., 58(4):707-715(1994)).

Kim et al describe a process for preparing ABA whose side chain is replaced with phenyl group; the process, however, accompanies highly complicate reaction steps. Further, the biological activity of ABA derivative prepared therefrom, is much lower than that of the natural ABA(see: B. T. Kim et al, Biosci. Biotech. Biochem., 56(4):624-629(1992)).

Nelson et al teach a process for preparing 7'-hydroxy abscisic acid; the process, however, not only requires expensive chemical reagents such as t-butyldimethylsilyl chloride, imidazole and tetrabutylaluminum fluoride, but also accompanies complex silylation and desilylation reaction steps. In addition, selective reduction of aldehyde group of α,β-unsaturated ketoaldehyde intermediate is performed only under specific conditions(see: L. A. K. Nelson et al, Tetrahedron, 47(20/21):3259-3270(1991)).

Rose et al demonstrate a process for preparing 7,7'-difluorinated ABA by the fluorination of ketoaldehyde with diethylaminosulphur trifluoride("DAST"); the process, however, also requires expensive reactants such as DAST, but also accompanies arduous fluornation step.

Under the circumstances, these prior art ABA derivatives have proven less satisfactory in the sense that they cannot be prepared in a practical manner and do not provide desired biological activity; and, therefore, there is a need in the art for the development of ABA derivative which possesses stable and steady biological activity and process for preparing same in a simple and economical manner.

SUMMARY OF THE INVENTION

In accordance with the present invention, the present inventors developed novel fluorinated abscisic acid derivatives by way of substitution of C-8' with fluorine, which provides a stable and steady activity for plant growth regulator. The inventors also developed a simple and economical process for preparing same.

A primary object of the present invention is, therefore, to provide novel fluorinated abscisic acid derivatives represented by formula of:

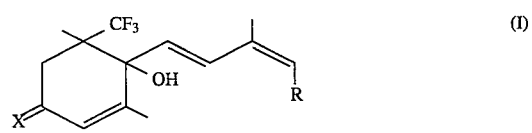

wherein:

X is O(CH$_2$)$_2$O or O; and,

R is hydroxymethyl, aldehyde, C$_{1-2}$ alkoxycarbonyl or carboxyl group.

The other object of the present invention is to provide novel process for preparing the fluorinated abscisic acid derivatives represented as the formula (I).

Another object of the invention is to provide novel plant growth regulators comprising the fluorinated abscisic acid derivatives represented as the formula (I).

DETAILED DESCRIPTION OF THE INVENTION

Fluorinated abscisic acid derivatives of the invention can be prepared by the following two-step processes, which should not be taken to limit the process of the invention.

Step I. Synthesis of 3,5-dimethyl-5-trifluoromethyl-1,1-ethylenedioxy- 2-cyclohexen-4-one Acetylmethylene triphenylphosphorane prepared from triphenylphosphine and chloroacetone, is dissolved in reaction solvent and synthesis of 4-trifluoromethyl-3-penten-2-one by reacting trifluoroacetone with the reaction mixture is followed. Ethyl acetoacetate is reacted with 4-trifluoromethyl- 3-penten-2-one in the presence of alkoxide base, to obtain 3,5-dimethyl-5-trifluoromethyl-2-cyclohexen-1-one as main product and 4-ethoxycarbonyl-3,5-dimethyl-5-trifluoromethyl- 2-cyclohexen-1-one as by-product respectively. Then, the main product is reacted with methylmagnesium iodide solution and ferric chloride to produce 3,5-dimethyl-5-trifluoromethyl- 3-cyclohexen-1-one. To the product thus obtained is added m-chloroperoxybenzoic acid and residue is obtained by distillation under reduced pressure. Alkaline solution is added to the residue to give 3,5-dimethyl-5-trifluoromethyl- 4-hydroxy-2-cyclohexen-1-one. Then, the resultant is dissolved in organic solvent, and Jones reagent and alcohol are added dropwise to the solution to obtain 3,5-dimethyl- 5-trifluoromethyl-2-cyclohexen-1,4-dione. Said compound is mixed with ethylene glycol, toluene and catalyst and heated under reflux to produce 3,5-dimethyl-5-trifluoromethyl- 1,1-ethylenedioxy-2-cyclohexen-4-one.

Step II. Synthesis of fluorinated abscisic acid derivative

Cis-3-methyl-2-penten-4-yn-1-ol is dissloved in organic solvent, and butyllithium is added dropwise to the solution in a slow stream of nitrogen. 3,5-dimethyl-5-trifluoromethyl- 1,1-ethylenedioxy-2-cyclohexen-4-one obtained in Step I is combined with the mixture, and sodium bis(2-methoxyethoxy)aluminum hydride is added dropwise to the reaction mixture to give the fluorinated abscisic acid derivative represented as the formula (I), where X is $O(CH_2)_2O$ and R is hydroxymethyl group. Manganese dioxide is reacted with the fluorinated abscisic acid obtained above to produce the fluorinated abscisic acid derivative represented as the formula (I), where X is $O(CH_2)_2O$ and R is aldehyde. To the fluorinated abscisic acid thus produced is added manganese dioxide, cyanide salt and acid to give the fluorinated abscisic acid derivative represented as the formula (I), where X is $O(CH_2)_2O$ and R is methoxycarbonyl. Mixture of organic solvent and acid is introduced into the fluorinated abscisic acid derivative, and is heated under reflux to produce the fluorinated abscisic acid derivative represented as the formula (I), where X is O and R is methoxy-carbonyl. The fluorinated abscisic acid thus produced is dissolved in an organic solvent and the base is added to the solution to give the fluorinated abscisic acid derivative represented as the formula (I), where X is O and R is carboxyl.

Step I and II are summarized as following Reaction Scheme 1 and 2.

Reaction Scheme 1:

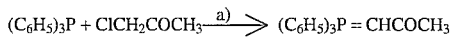

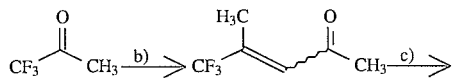

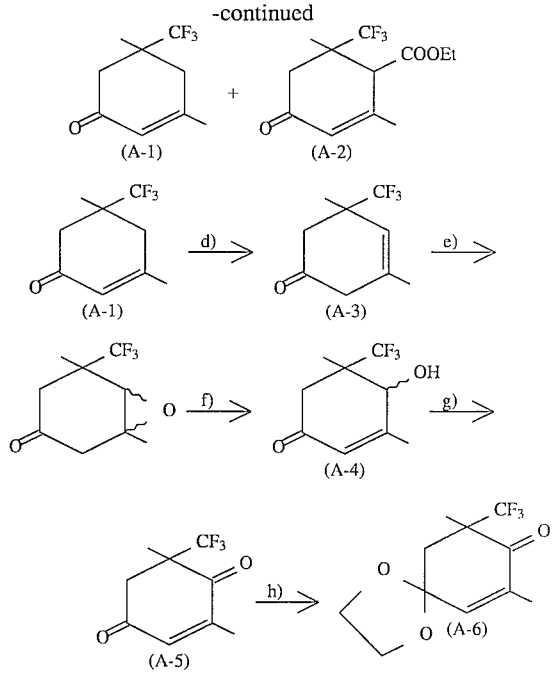

wherein:

a) is $CHCl_3$ and NaOH; b) is $(C_6H_5)_3P=CHCOCH_3$ and $CH_2Cl_2$; c) is ethyl acetoacetate, EtONa and EtOH; d) is $CH_3MgI$, $FeCl_3$ and ether; e) is m-CPBA and $CHCl_3$; f) is NaOH and $H_2O$; g) is $CrO_3$, $H_2SO_4$ and acetone; and, h) is ethylene glycol, p-TsOH and toluene.

Reaction Scheme 2:

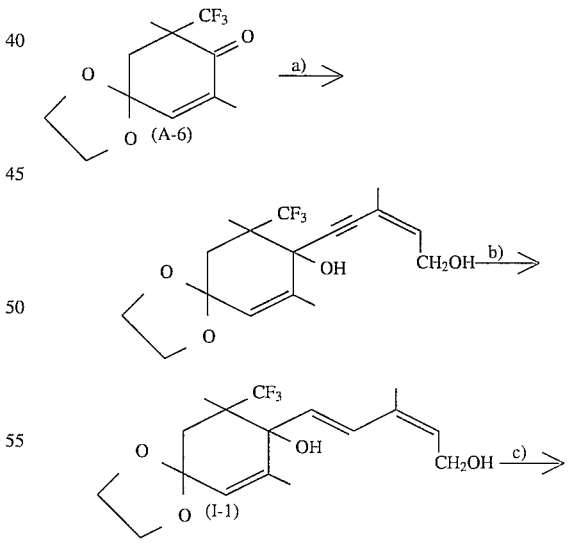

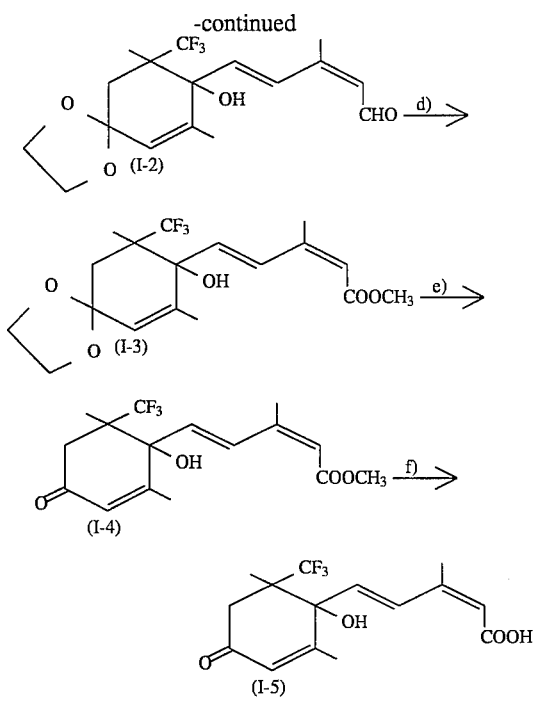

wherein:
a) is cis-3-methyl-2-penten-4-yn-1-ol, 2eq. BuLi and THF; b) is Redal™[sodium bis(2-methoxyethoxy) aluminum hydride] and THF; c) is $MnO_2$ and acetone; d) is $MnO_2$, NaCN, AcOH and $CH_3OH$; e) is $H_2SO_4$, THF and $H_2O$; and, f) is NaOH, $CH_3OH$ and $H_2O$.

Reaction conditions are indicated in the above Reaction Scheme 1 and 2. Organic solvent and mixture thereofs which do not affect badly on the reaction can be employed in the reaction; and, proper temperature and time can be applied in the reaction within their range generally used in chemical reaction. Furthermore, oxidizing/reducing agents, acids/bases and catalysts employed in the reaction can be replaced with another functionally equivalent reagents.

The fluorinated abscisic acid derivatives represented as the formula (I) can be isolated or purified by means of the known techniques in the art, e.g., distillation, crystallization and chromatography in accordance with their specific physicochemical character; and, identified by the spectrometric methods employing $^1$H-NMR and mass spectrometry, etc.

The fluorinated abscisic acid derivative (I) prepared by the present invention possesses more stable and steady biological activity than natural ABA; and, therefore, they can be applied as active ingredients for plant growth regulators such as germination inhibitor, growth retardant and lodging repressor, etc., or intermediates therefor.

The present invention is further illustrated in the following examples, which should not be taken to limit the scope of the invention.

EXAMPLE 1

Preparation of acetylmethylene triphenylphosphorane

In a dried flask, 131.15 g (0.5 mole) of triphenylphosphine and 47.2 g (0.51 mole) of chloroacetone were dissolved in 300 ml of chloroform and heated under reflux for 20 hrs. The reaction mixture was cooled to room temperature and the solvent was evaporated under reduced pressure. The residue was added to 1L of water and 5N sodium hydroxide was added to the mixture. Solid substance thus formed was extracted with methylene chloride, and dried using anhydrous magnesium sulfate. The residue where the organic solvented was removed, was washed with n-hexane and dried under vacuum to give 143.1 g of the title compound(yield: 90%). Chemical analysis was performed to identify the desired compound by $^1$H-NMR spectroscopy.

$^1$H-NMR(CDCl$_3$, TMS) δ: 2.08(d, 3H), 7.20–7.60(m, 16H)

EXAMPLE 2

Preparation of 4-trifluoromethyl-3-penten-2-one

In a dried 500 ml 3-neck flask equipped with dry ice-cooler, 79.5 g (0.25 mole) of acetylmethylene triphenylphosphorane prepared in Example 1 was dissolved in 150 ml of dried methylene chloride, and 28 g (0.25 mole) of trifluoroacetone was added dropwise. The reaction mixture was stirred for 18 hrs at room temperature and filtrated. The filtrate was subject to simple distillation, and the residue obtained was washed with pentane. The solution obtained from washing was distilled again to give 32 g of the title compound(yield: 84%).

b.p.: 106°–108° C.

$^1$H-NMR(CDCl$_3$, TMS) δ: 2.20(s, 3H), 2.32(s, 3H), 6.63 (m, 1H)

MS m/e(rel. int.): 152(M$^+$, 14), 137(54), 132(9), 109(6), 89(46), 75(6), 69(9), 59(18), 43(100)

EXAMPLE 3

Preparation of 3,5-dimethyl-5-trifluoromethyl-2-cyclohexen- 1-one (A-1)

In a dried 100 ml 3-neck flask, 15.2 g(0.1 mole) of 4-trifluoromethyl- 3-penten-2-one prepared in Example 2, 13 g(0.1 mole)of ethyl acetoacetate and 3.4 g of sodium ethoxide were added to 60 ml of benzene, and stirred for 4 hrs at 60° C. The reaction mixture was cooled to room temperature and water was added. After neutralization using 10N hydrochloric acid solution, the organic layer was extracted, and dried over magnesium sulfate. The residue was distilled under the vacuum pressure of 1 mmHg, to obtain 11.2 g of the title compound as main product(yield: 58.3%) and 4.5 g of 4-ethoxycarbonyl-3,5-dimethyl- 5-trifluoromethyl-2-cyclohexen-1-one(A-2) as by-product(yield: 17%).

main product: 3,5-dimethyl-5-trifluoromethyl-2-cyclohexen-1-one(A- 1)

b.p.: 79°–83° C.

$^1$H-NMR(CDCl$_3$, TMS) δ: 1.27(s, 3H), 2.07(s, 3H), 2.33–2.74(m, 4H), 6.13(bs, 1H)

MS m/e(rel. int.): 192(M$^+$, 90), 130(11), 95(15), 88(23), 82(100), 54(72), 43(100) by-product: 4-ethoxycarbonyl-3, 5-dimethyl-5-trifluoromethyl-2-cyclohexen-1-one (A-2)

$^1$H-NMR(CDCl$_3$, TMS) δ: 1.28(s, 3H), 1.31(t, 3H), 1.98 (s, 3H), 2.58(d, 1H, J=17.3 Hz), 2.75(d, 1H, 17.3 Hz), 3.54(s, 1H), 4.25(q, 2H), 6.04(s, 1H)

MS m/e(rel. int.): 264(M$^+$, 91), 219(16), 191(70), 177(39), 163(22), 154(52), 123(100)

EXAMPLE 4

Preparation of 3,5-dimethyl-5-trifluoromethyl-3-cyclohexen-1-one (A-3)

In a dried flask, 1.17 g(48 mmole) of magnesium was added to 20 ml of dried ether in a stream of nitrogen, and to the reaction mixture was added in dropwise 2.99 ml(48 mmole) of iodomethane dissolved in 3 ml of ether, while cooling the flask, to produce solution of methylmagnesium iodide. 0.065 g of ferric chloride was added to the solution, and 7.68 g(40 mmole) of 3,5-dimethyl-5-trifluoromethyl-2-cyclohexen-1-one(A-1) dissolved in 6 ml of ether was added dropwise for 20 minutes, while cooling the flask. After heating under reflux, the solution was stirred for 10 minutes and was added to the 50 ml of ice water. The resultant was acidified using dilute acetic acid, and extraction was followed to form organic layer. The organic layer thus formed was dried over anhydrous magnesium sulfate to remove the solvent. Then, the residue was fractionated by the aid of column chromatograpy employing hexane/ethyl acetate(4:1, v/v) as eluent to give 5.4 g of the title compound(yield: 70.3%).

$^1$H-NMR(CDCl$_3$, TMS) δ: 1.25(s, 3H), 2.08(s, 3H), 2.35–2.92 (m, 4H) , 6.16 (bs, 1H)

MS m/e(rel. int.): 192(M$^+$, 91), 110(8), 95(13), 82(100), 54(66)

EXAMPLE 5

Preparation of 3,5-dimethyl-5-trifluoromethyl-4-hydroxy-2-cyclohexen-1-one (A-4)

5.3 g (27.6 mmole) of 3,5-dimethyl-5-trifluoromethyl-3-cyclohexen-1-one(A-3) prepared in Example 4 and 9.53 g (55.2 mmole, purity: 50%) of m-chloroperoxybenzoic acid(m-CPBA) were combined with 100 ml of chloroform, stirred for 20 hrs at room temperature, and the reaction mixture was filtrated. The resultant thus filtrated was evaporated under reduced pressure, was washed with n-hexane, and evaporated again under reduced pressure. To the residue were added 20 ml of ether and 10 ml of water, and the acidity of the solution was adjusted to the pH value of 11 to 12 using aqueous sodium hydroxide. The reaction mixture was stirred for 3 hrs at room temperature and the organic layer was extracted twice with 20 ml of ether, and dried over anhydrous magnesium sulfate. The residue where the organic solvent was removed, was fractionated with column chromatography using n-hexane/ethyl acetate(2:1 , v/v) as eluent to give 4.42 g of the title compound(yield: 77%).

$^1$H-NMR(CDCl$_3$, TMS) δ: 1.23(s, 3H), 1.06(d, 3H, J=1.3 Hz), 2.53(d, 2H, J=4.5 Hz), 3.31(bs, 1H, OH), 4.77(s, 1H), 5.92(s, 1)

MS m/e(rel. int.): 208(M$^+$, 16), 166(47), 131(9), 98(100), 97(42), 82(23), 69(89)

EXAMPLE 6

Preparation of 3,5-dimethyl-5-trifluoromethyl-2-cyclohexen-1,4-dione (A-5)

In the 20 ml of acetone was dissolved 3,5-dimethyl-5-trifluoromethyl- 4-hydroxy-2-cyclohexen-1-one(A-4) prepared in Example 5, and 6.2 ml of Jones reagent was added dropwise. Then, the mixture was stirred for 10 minutes, was added dropwise to 10 ml of methyl alcohol and stirred for 30 minutes. The reaction mixture was filtered to remove the filtrate. The residue thus obtained was fractionated with column chromatography using n-hexane/ethyl acetate(4:1, v/v) as eluent to give 2.74 g of the title compound(yield: 86.4%).

$^1$H-NMR(CDCl$_3$, TMS) δ: 1.48(s, 3H), 2.05(d, 3H, J=1.5 Hz), 2.97 (q, 2H, J=17.2 Hz, J=50.4 Hz), 6.68 (d, 1H, J=1.5 Hz)

MS m/e(rel. int.): 206(M$^+$, 87), 91(6), 179(61), 164(40), 137(100), 109(50), 68(100)

EXAMPLE 7

Preparation of 3,5-dimethyl-5-trifluoromethyl-1,1-ethylenedioxy-2-cyclohexen-4-one (A-6)

2.64 g (12.8 mmole) of 3,5-dimethyl-5-trifluoromethyl-2-cyclohexen- 1,4-dione(A-5) prepared in Example 6 and 1.59 g (25.6 mmole) ethylene glycol were mixed with 250 ml of toluene, and 0.1 g of p-toluenesulfonic acid was added as catalyst. After cooling to room temperature, the reaction mixture was washed with water and aqueous solution of sodium bicarbonate. The organic layer thus formed was dried using anhydrous magnesium sulfate and the solvent was evaporated under reduced pressure. The residue was fractionated with column chromatography using n-hexane/ethyl acetate(5:1, v/v) as eluent to produce the title compound(yield: 90.6%).

$^1$H-NMR(CDCl$_3$, TMS) δ: 1.53(s, 3H), 1.87(s, 3H), 2.41(q, 2H), 4.01(s, 4H), 6.43(M, 1H)

MS m/e(rel. int.): 250(M$^+$, 4), 222(100), 207(23), 185(5), 181(21), 153(24), 140(100), 137(16), 126(81), 112(100), 86(57), 68(86)

EXAMPLE 8

Preparation of 5-(2',6'-dimethyl-6'-trifluoromethyl-4',4'-ethylenedioxy-1'-hydroxy-2'-cyclohexen-1'-yl)-3-methyl-2-penten-4-yn-1-ol 770 ml (8 mmole) of cis-3-methyl-2-penten-4-yn-1-ol was added to the 60 ml of dried tetrahydrofuran(THF) under the blanket of dry nitrogen, cooled to −78° C. and 6.4 ml(16 mmole) of 2.5M n-butyllithium was added dropwise to the reaction solution. The reaction mixture was heated slowly to the temperature of 0° C., chilled again to −78° C. and 2 g (8 mmole) of 3,5-dimethyl-5-trifluoromethyl- 1,1-ethylenedioxy-2-cyclohexen-4-one(A-6) dissolved in 5 ml of THF was added dropwise. The resultant thus formed was heated slowly to room temperature, mixed with water, and the organic layer was extracted with ethyl acetate and dried over magnesium sulfate. The residue where the organic layer was removed, was fractionated with column chromatography employing n-hexane/ethyl acetate(2:1, v/v) as eluent to give 2.3 g of thr title compound(yield: 83%).

$^1$H-NMR(CDCl$_3$, TMS) δ: 1.40(s, 3H), 1.87(s, 3H), 1.97(s, 3H), 2.10–2.60(m, 4H), 3.93(s, 4H), 4.33(d, 2H), 5.47(s, 1H), 5.90(m, 1H)

MS m/e(rel. int.): 346(M$^+$, 5), 329(46), 242(26), 236(45), 218(18), 191(17), 175(17), 147(22), 117(12), 87(100), 73(11)

EXAMPLE 9

Preparation of
5-(2',6'-dimethyl-6'-trifluoromethyl-4',4'-ethylenedioxy-1'-hydroxy-2'-cyclohexen-1'-yl)-3-methyl-2,4-pentadien-1-ol (I-1)

1.211 g (3.5 mmole) of 5-(2',6'-dimethyl-6'-trifluoromethyl- 4',4'-ethylenedioxy-1'-hydroxy-2'-cyclohexen-1'-yl)-3-methyl-2-penten- 4-yn-1-ol prepared in Example 8 was dissolved in 50 ml of dried tetrahydrofuran, and cooled to −10° C. 3.1 ml of Redal™[sodium bis(2-methoxyethoxy)aluminum hydride] was added dropwise to the reaction mixture, and stirred for 4 hrs. To the reaction mixture was added dropwise 6 ml of water, and extracted with ether. The extract was dried over magnesium sulfate, and organic solvent was removed. The residue was fractionated with column chromatography using a mixture of n-hexane and ethyl acetate(1:1, v/v) as eluent to produce 0.95 g of the title compound(yield: 78%).

$^1$H-NMR(CDCl$_3$, TMS) δ: 1.27(s, 3H), 1.70(s, 3H), 1.89(s, 3H), 2,10–2.83 (m, 4H), 3.99 ( s, 4H), 4.23(d, 2H), 5.49–6.01(m, 3H), 6.85(d, 1H)

MS m/e(rel. int.): 348(M$^+$, 5), 331(25), 287 (59), 259(21), 176(58), 149(100), 135(20), 107(66), 96(38), 69(10)

EXAMPLE 10

Preparation of 5-(2',6'-dimethyl-6'-trifluoromethyl-4',4'-ethylenedioxy-1'-hydroxy-2'-cyclohexen-1'-yl)-3-methyl-2,4-pentadiene-1-aldehyde (I-2)

With 70 ml of acetone was mixed 1.22 g(3.5 mmole) of 5-( 2',6'-dimethyl-6'-trifluoromethyl-4',4'-ethylenedioxy-1'-hydroxy- 2'-cyclohexen-1'-yl)-3-methyl-2,4-pentadien-1-ol(I-1) prepared in Example 9 and 3.04 g (0.035 mole) of manganese dioxide. The mixture was stirred for 1 hr at room temperature, and filtered. The residue where the filtrate was evaporated under reduced pressure, was purified with column chromatography employing n-hexane/ethyl acetate(2:1, v/v) as eluent to give 1.09 g of the title compound(yield: 90%).

$^1$H-NMR(CDCl$_3$, TMS) δ: 1.27(s, 3H), 1.68(s, 3H), 2.07(d, 3H), 2.0–2.5 (m, 3H), 3,99 ( s, 4H), 5.61(s, 1H), 6.01(m, 1H), 6.17(d, 1H), 7.49(d, 1H), 10.30(d, 1H)

MS m/e(rel. int.): 346(M$^+$, 3), 329(38), 300(21), 286(50), 217 (48), 177 (65), 149(100), 81(29)

EXAMPLE 11

Preparation of methyl
5-(2',6'-dimethyl-6'-trifluoromethyl-4',4'-ethylenedioxy-1'-hydroxy-2'-cyclohexen-1'-yl)-3-methyl-2,4-pentadienoate(I-3)

0.692 g (2 mmole) of 5-(2',6'-dimethyl-6'-trifluoromethyl-4',4'-ethylenedioxy-1'-hydroxy-2'-cyclohexen-1'-yl)-3-methyl-2,4-pentadiene-1-aldehyde(I-2) prepared in Example 10, 2.6 g(30 mmole) of manganese dioxide, 0.245 g(5 mmole) of sodium cyanide and 0.12 ml of acetic acid were mixed with 20 ml of methyl alcohol, and stirred for 2 hrs at room temperature. The reaction mixture was filtrated, evaporated under reduced pressure. Water and ether were added to the residue thus filtered, the organic layer was extracted with ether, and washed with saturated saline. Washings were dried over anhydrous magnesium sulfate, and the solvent was evaporated under reduced pressure.

Fractionation of the residue by column chromatography using n-hexane/ethyl acetate(2:1, v/v) gave 0.52 g of the title compound(yield: 69%).

m.p.: 125°–126° C.

$^1$H-NMR(CDCl$_3$, TMS) δ: 1.26(s, 3H), 1.95(d, 3H), 2.05(d, 3H), 2.48(d, 1H), 2.75(bs, 1H), 2.89(d, 1H), 3.71(s, 3H), 3.99(s, 4H), 5.78(s, 1H), 5.95(s, 1H), 6.01 (d, 1H), 7.92(d, 1H)

MS m/e(rel. int.): 376(M$^+$, 5), 360(6), 303(23), 258(17), 193(25), 190(70), 181(11), 172(11), 162(10), 125(100), 112(18), 87(100)

EXAMPLE 12

Preparation of methyl
5-(2',6'-dimethyl-6'-trifluoromethyl-4'-oxo-1'-hydroxy-2'-cyclohexen-1'-yl)-3-methyl-2,4-pentadienoate (I-4)

0.34 g (0.9 mmole) of 5-(2',6'-dimethyl-6'-trifluoromethyl-4',4'-ethylenedioxy-1'-hydroxy-2'-cyclohexen-1'-yl)-3-methyl- 2,4-pentadienoate(I-3) prepared in Example 11 was added to the mixture of 10 ml of tetrahydrofuran and 10 ml of 20 wt % sulfuric acid, and heated under reflux for 1 hr. The mixture was cooled, extracted with 20 ml of ether, and dried over anhydrous magnesium sulfate. After solvent was removed, the residue was purified with column chromatography using n-hexane/ethylacetate (2:1, v/v) to give 0.27 g of the title compound(yield: 90%).

$^1$H-NMR(CDCl$_3$, TMS) δ: 1.60(s, 3H), 1.97(s, 3H), 2.03(s, 3H), 2.28–3.10(m, 3H) , 3.70(s, 3H), 5.83(s, 1H), 6.03(s, 1H), 6.07(d, 1H), 7.93(d, 1H)

MS m/e(rel. int.): 332(M$^+$, 5), 300(20), 272(19), 259(59), 190(100), 162(100), 151(35), 125(100)

EXAMPLE 13

Preparation of (±) 8',8',8'-trifluoroabscisic acid (I-5)

0.2 g (0.6 mmole) of methyl 5-(2',6'-dimethyl-6'-trifluoromethyl- 4'-oxo-1'-hydroxy-2'-cyclohexen-1'-yl)-3-methyl-2,4-pentadienoate(I- 4) prepared in Example 12 was dissolved in 5 ml of methyl alcohol. 0.41 g of sodium hydroxide dissolved in 5 ml of water was added to the mixture, and was heated under reflux for 1 hr. Ethyl alcohol was evaporated under reduced pressure, and the reaction mixture was acidified with 2N hydrochloric acid. The reaction mixture thus acidified was extracted with 20 ml of ethyl acetate, and dried over anhydrous magnesium sulfate. The residue where the organic solvent was removed, was fractionated with column chromatography using solvent mixture of n-hexane/ethyl acetate/formic acid(50:50:0.2, v/v/v) to give 0.13 g of the title compound(yield 68%).

$^1$H-NMR (CDCl$_3$+Methanol-d$_4$, TMS ) δ : 1.27(s, 3H), 1.97(s, 3H), 2.04(s, 3H), 2.54 (d, 1H, J=17.6 Hz), 2.81(d, 1H, J=16.9 Hz), 5.80(s, 1H), 5.98(s, 1H), 6.07(d, 1H, J=16.1 Hz), 7.79 (d, 1H, J=16 Hz)

MS m/e(rel. int.): 318(M$^+$, 22), 301(80), 272(13), 259(69), 231(11), 221(100), 208(43), 190(85), 162(52), 147(12), 134(76), 111(100), Biological Activity of the Fluorinated ABA Derivatives The fluorinated ABA derivatives of the invention(hereinafter referred to as "the fluorinated ABA") can be applied as agrochemicals for various plant growth regulation, e.g., germination inhibitors, growth retardants such as herbicide and lodging repressors such as dwarfing agent.

Plant growth regulator comprising the fluorinated ABA, is generally formulated in a form of aqueous solution; and, applied or treated to the plants/field in a direct/indirect manner. The plant growth regulator can be used as a herbicide or dwarfing agent in a mixed form with commercial herbicide or dwarfing agent; and, it can also be used as a formulation comprising antimicrobial agent or insecticide for plants in the art.

The kind of applicable plants and site thereofs, and application stage, method, amount and formulation type for the plant growth regulator comprising the fluorinated ABA, are illustrated in Table 1 below.

TABLE 1

Application of the plant growth regulator comprising the fluorinated ABA

| Use Application Condition | Use of the plant growth regulator | |
|---|---|---|
| | Herbicide | Dwarfing agent |
| Applicable plant | all herbaceous plants | annual plants |
| Applied site | plant seed or foliar leaf region | |
| Application stage of growth | identical with conventional herbicides | sowing, infant-germ, maturation stage |
| Application method | ground spray | ground spray or soil mixing |
| Application amount (per 1 m² ground) | over 0.01 mg | 0.01 to 1 mg |
| Formulation type | wettable power (WP), emulsifiable concentrate (EC), dusts and so on | |

Biological activities of the fluorinated ABA are tested, in view of inhibitory activities for germination, α-amylase induction and elongation; and, comparision with those of natural ABA was followed. The following tests were made to determine said inhibitory activities.

1. Germination Inhibition Test

To the fluorinated ABA was added ethyl alcohol, and, the solution was added dropwise over a filter paper on petri dish(diameter 6 cm), and dried in the air. 1 ml of distilled water was added to another petri dish, and the above dried paper was put on the petri dish. Then, on the petri dish, twenty five seeds of cress(*Lepidium sativum*) were loaded; and, incubated at 25° C. for 36 hrs under dark condition. The number of non-germinated seeds was counted and compared with that of control. The half germination inhibition($pI_{50}$) for the fluorinated ABA of the invention was determined-(see: Table 2). All tests were made in triplicate in the range of 0.3 to 1 ppm of the fluorinated ABA.

TABLE 2

Germination inhibition activity of the fluorinated ABA

| Compound | Half germination inhibition ($pI_{50}$) |
|---|---|
| I-1 | 5.62 |
| I-2 | 5.98 |
| I-3 | 5.24 |
| I-4 | 6.08 |
| I-5 | 5.96 |
| Natural ABA | 6.08 |

2. α-Amylase Induction Inhibition Test
2-1. Preparation of α-amylase Containing Solution Barley(*Hordeum vulgare* L. var, *hexastichon*) seeds were sterilized and halved. To sterile 2 ml medium(1 mM acetate buffer containing 20 μM $CaCl_2$, pH 5.1), were added ten of halved seeds containing albumen, and addition of the fluorinated ABA solution was followed. The halved barley seeds were incubated with $GA_3$(Gibberellic acid) at 25° C. for 48 hrs to promote α-amylase synthesis, homogenated, washed with 3 ml of said medium, and centrifuged at 2000 g for 10 min. The pellet thus obtained was suspended with 3 ml of the acetate buffer solution and centrifugated again. Supernatants thus obtained were pooled and adjusted to a volume of 10 ml with distilled water; and, employed for determination of α-amylase activity.

2-2. α-Amylase Activity Determination

On the above solution comprising α-amylase("enzyme solution"), α-amylase activity was determined in accordance with the method described below, and compared with that of natural ABA: 100 mg of starch was dissolved in 10 ml of distilled water to prepare substrate for α-amylase. 0.05% iodine($I_2$) solution containing 0.05N-HCl was employed for termination of α-amylase reaction and for development of the color. For the determination of α-amylase activity, 0.5 ml of the substrate, 1 ml of enzyme solution and 0.5 ml of 0.1M acetate buffer(containing 20 mM $CaCl_2$, pH 5.1) were combined, and incubated at 30° C. for 5 min. The reaction was blocked by the temination solution with immediate chilling. After addition of distilled water, optical density(O.D) at 620 nm was measured to determine α-amylase activities for the fluorinated and natural ABA, based on the standard calibration curve of enzyme activity(see: Table 3).

TABLE 3

α-Amylase induction inhibition activity of the fluorinated ABA

| Compound | α-Amylase induction inhibition activity |
|---|---|
| I-1 | ++ |
| I-2 | ++ |
| I-3 | ++ |
| I-4 | ++ |
| I-5 | +++ |
| Natural ABA | +++ |

3. Elongation Inhibition Test

After 10 infant rice plants were inoculated on the pots containing medium, the fluorinated ABA was ground-sprayed in a constant concentration. After the pots were covered with vinylon to prevent evaporation of water, the infant rice plants were incubated for 10 days at 25°–30° C., and length of the infant rice leaves was measured(see: Table 4). A series of tests were made in the range of 0.3 to 1 ppm of the fluorinated ABA.

TABLE 4

Elongation inhibition activity of the fluorinated ABA

| Compound | Elongation inhibition activity |
|---|---|
| I-1 | ++ |
| I-2 | ++ |
| I-3 | ++ |
| I-4 | ++ |
| I-5 | +++ |
| Natural ABA | +++ |

As shown in the Tables 2–4 above, it was determined that: inhibitory activities of the fluorinated ABA for germination, α-amylase induction and elongation of the plants were substantially equivalent to or higher than those of natural ABA. Accordingly, it is clearly demonstrated that the fluorinated ABA can be applied as a potent growth regulator for plants in a practical manner.

As clearly illustrated and demonstrated as aboves, the present invention provides novel fluorinated ABA derivatives, process for preparing same and their use for plant growth regulators. The fluorinated ABA prepared by the present invention possesses more stable and steady biological activity than natural ABA; and, therefore, they can be applied as active ingredients for plant growth regulators such as germination inhibitor, growth retardant and lodging repressor, etc., or intermediates therefor.

What is claimed is:

1. Fluorinated abscisic acid derivative represented by the formula of:

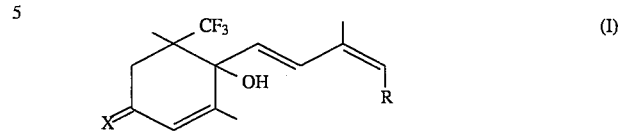

wherein:

X is $O(CH_2)_2O$ or $O$; and,

R is hydroxymethyl, aldehyde, $C_{1-2}$ alkoxycarbonyl or carboxyl group.

2. Plant growth regulator comprising the fluorinated abscisic acid derivative of claim 1 as an active ingredient.

* * * * *